(12) United States Patent
Spyrou et al.

(10) Patent No.: US 8,846,979 B2
(45) Date of Patent: Sep. 30, 2014

(54) USE OF β-ISOPHORONE AS SOLVENT

(75) Inventors: Emmanouil Spyrou, Schermbeck (DE); Lars Hellkuhl, Gescher (DE); Marina Grammenos, Duesseldorf (DE); Andrea Henschke, Duelmen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/704,465

(22) PCT Filed: Jun. 7, 2011

(86) PCT No.: PCT/EP2011/059325
§ 371 (c)(1),
(2), (4) Date: Dec. 14, 2012

(87) PCT Pub. No.: WO2012/004073
PCT Pub. Date: Jan. 12, 2012

(65) Prior Publication Data
US 2014/0005438 A1    Jan. 2, 2014

(30) Foreign Application Priority Data
Jul. 6, 2010 (DE) .......... 10 2010 030 995

(51) Int. Cl.
| C07C 49/603 | (2006.01) |
| A01N 47/10 | (2006.01) |
| C09D 7/00 | (2006.01) |
| A01N 25/02 | (2006.01) |

(52) U.S. Cl.
CPC .............. *C07C 49/603* (2013.01); *C09D 7/001* (2013.01); *A01N 25/02* (2013.01)
USPC .......................................... 568/377; 504/143

(58) Field of Classification Search
USPC .......................................... 568/377; 504/143
See application file for complete search history.

(56) References Cited

U.S. PATENT DOCUMENTS

| 3,397,120 A | 8/1968 | William et al. |
| 4,046,813 A | 9/1977 | Brenner |
| 6,255,509 B1 | 7/2001 | Takahashi et al. |

FOREIGN PATENT DOCUMENTS

| CN | 101182288 A | 5/2008 |
| GB | 2 243 551 | 11/1991 |

OTHER PUBLICATIONS

Quarles, R., "Ketones as Solvents for VINYL RESINS," Industrial and Engineering Chemistry, vol. 35, No. 10, pp. 1033 to 1043, (Oct. 1943).
International Search Report Issued Dec. 23, 2011 in PCT/EP11/59325 Filed Jun. 7, 2011.
Combined Chinese Office Action and Search Report issued Nov. 15, 2013 in Patent Application No. 201180032964.9 (with English language translation).
Huang Yuwei, et al., "Research the chemical equilibrium and reaction kinetics of isomerization of β-isophorone to α-isophorone", Chemical Engineering and Equipment, No. 5, Oct. 15, 2007, pp. 9-11 (with English language translation).
Guan Xu, et al., "Production, market and application prospect of isophorone", Chemical Technology Market, No. 8, Aug. 12, 2005, pp. 5-8 (with English abstract).

*Primary Examiner* — Sikarl Witherspoon
(74) *Attorney, Agent, or Firm* — Oblon, Spivak, McClelland, Maier & Neustadt, L.L.P.

(57) ABSTRACT

The invention relates to the use of β-isophorone as solvent.

12 Claims, No Drawings

USE OF β-ISOPHORONE AS SOLVENT

The invention relates to the use of β-isophorone as solvent.

Isophorone, also called α-isophorone, is used as a solvent on account of its outstanding dissolution properties and its favorable price, and is used primarily in the field of crop protection compositions (see, for example, CN 101569312, RU 2263449, DE 32 25 940, U.S. Pat. No. 3,281,234, U.S. Pat. No. 3,253,021), but also in the context of various large-scale industrial coating processes, such as in coil coating.

The use of isophorone nowadays, however, is restricted, because isophorone is classed as potentially hazardous from a toxicological standpoint, and carries the R-phase R 40 (limited evidence of a carcinogenic effect). The reason for this limited evidence might lie in the structure of isophorone—to be more precise, in the α,β-unsaturated carbonyl moiety. Such moieties are known in general to carry the risk of a carcinogenic effect.

Accordingly there has in the past been no lack of attempts to replace isophorone by other solvents. However, either the dissolution properties have not been sufficient (e.g., 3,3,5-trimethylcyclohexanone), or the boiling point has been too different, or the alternatives have been simply too costly.

It was an object of the present invention to provide suitable substitutes for isophorone. Surprisingly it has been found that an isomer of α-isophorone, namely β-isophorone, possesses the required qualities.

The invention provides for the use of β-isophorone as a solvent, more particularly as a solvent for crop protection compositions, and also for large-scale industrial coating operations, such as coil coating. Additionally provided by the present invention is the use of β-isophorone in coating materials, more particularly in primers, topcoats, clearcoats, adhesives or sealing materials.

β-Isophorone has to date been used exclusively as an intermediate, such as in the synthesis of ketoisophorone (e.g., EP 808 816), which is a starting component for the synthesis of vitamin E, for example.

β-Isophorone differs from α-isophorone in the position of the double bond. In α-isophorone, the double bond is in conjugation with the carbonyl moiety, whereas in β-isophorone it is at a greater distance. Consequently there is no longer a likelihood of unwanted Michael addition reactions, which are known to be held responsible for carcinogenic effects.

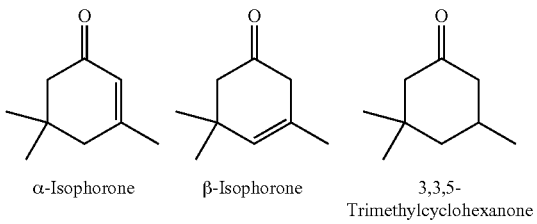

α-Isophorone     β-Isophorone     3,3,5-Trimethylcyclohexanone

β-Isophorone can be prepared inexpensively with an almost 100% yield from α-isophorone by a simple rearrangement and by distillative isolation. This is recorded by a whole series of patent specifications and other references (e.g., CN 1660752, EP 1 063 220, EP 1 063 219, EP 957 075, JP 11/255706, JP 11/049712, EP 842 918, DE 196 39 570, EP 488 045, DE 37 35 211, Journal of Organic Chemistry (1978), 43(9), 1821-3).

Compared with α-isophorone, β-isophorone has very similar dissolution properties (see experimental section), as evident not least by the octanol-water partition coefficient (log P value): α-isophorone is situated at 1.7, β-isophorone at 1.4, whereas a conventional substitute such as 3,3,5-trimethylcyclohexanone (TMC-one) is at 2.5.

It is preferred to use a β-isophorone purity of >95% by weight, more preferably >98% by weight, and very preferably >99% by weight.

The experimental section is intended to demonstrate that the dissolution properties of β-isophorone are similar to those of α-isophorone, especially in respect of the two crop protection agents most commonly dissolved in α-isophorone, namely PROPANIL and PHENMEDIPHAM, which are presently dissolved to up to 55% by weight in α-isophorone.

EXPERIMENTAL SECTION

Substances Used:
α-Isophorone: boiling point 215° C., Evonik-Degussa GmbH
β-Isophorone: boiling point 190° C., prepared from α-isophorone (DE 198 21 379, Degussa)
TMCone: boiling point 188-192° C., Evonik-Degussa GmbH
PROPANIL: Schirm
PHENMEDIPHAM: Chemos General Operating Instructions:

70 parts of PHENMEDIPHAM or PROPANIL were introduced into 30 parts of the solvent, followed by thorough stirring. After 2 hours of stirring, the residue was removed by centrifugation and the supernatant clear solution was weighed out into a round-bottom flask. The solvent was distilled off completely at 0.06 mbar and 130° C., and the round-bottom flask was reweighed. The solubilities found for the different solvents were as follows (in % by weight):

|  | α-Isophorone* | β-Isophorone | TMC-one* |
| --- | --- | --- | --- |
| PHENMEDIPHAM | 58% | 55% | 50% |
| PROPANIL | 65% | 56% | 58% |

*noninventive, comparative examples

Only α-isophorone and β-isophorone dissolve the two most common crop protection agents, PHENMEDIPHAM and PROPANIL, equally to at least 55% by weight. TMC-one dissolves PROPANIL, but not Phenmedipham, to 55% by weight. Consequently, β-isophorone is a suitable substitute for α-isophorone.

The invention claimed is:

1. A method of coating an article, the method comprising: applying a composition comprising β-isophorone to the article.

2. The method of claim 1, wherein the article is a coil.

3. A method of crop protection, comprising: providing a solvent comprising β-isophorone to a crop.

4. The method of claim 1, wherein the composition is a primer, a topcoat, an adhesive, or a sealing material.

5. The method of claim 1, wherein a purity of β-isophorone in the composition is greater than 95% by weight in total.

6. The method of claim 3, wherein a purity of β-isophorone in the composition is greater than 95% by weight in total.

7. The method of claim 1, wherein a purity of β-isophorone in the composition is greater than 98% by weight in total.

8. The method of claim 3, wherein a purity of β-isophorone in the composition is greater than 99% by weight in total.

9. The method of claim 1, wherein the composition further comprises methyl 3-(3-methylcarbaniloyloxy)carbanilate.

10. The method of claim 1, wherein the composition further comprises N-(3,4-Dichlorophenyl)propanamide.

11. The method of claim 3, wherein methyl 3-(3-methylcarbaniloyloxy)carbanilate is dissolved in the solvent.

12. The method of claim 3, wherein N-(3,4-Dichlorophenyl)propanamide is dissolved in the solvent.

\* \* \* \* \*